US00PP26243P2

(12) United States Plant Patent
Probst

(10) Patent No.: US PP26,243 P2
(45) Date of Patent: Dec. 15, 2015

(54) ***LYCHNIS* PLANT NAMED 'LIPSTICK'**

(50) Latin Name: *Lychnis sieboldii*
Varietal Denomination: Lipstick

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 73 days.

(21) Appl. No.: 13/999,462

(22) Filed: Mar. 3, 2014

Related U.S. Application Data

(60) Provisional application No. 61/852,378, filed on Mar. 15, 2013.

(51) Int. Cl.
*A01H 5/00* (2006.01)

(52) U.S. Cl.
USPC ..... Plt./452

(58) Field of Classification Search
USPC ..... Plt./452
See application file for complete search history.

*Primary Examiner* — Annette Para
(74) *Attorney, Agent, or Firm* — Penny J. Aguirre

(57) ABSTRACT

A new cultivar of *Lychnis*, 'Lipstick', characterized by its sturdy and well-branched erect stems up to 45 cm in height, its large flowers that are red in color, its red flowers that are large in comparison to the species, its foliage that is red-purple in color when young and mature to dark green suffused with purple with the purple coloration maintained well into the season, its long-lived habit and its reliable cold hardiness at least to U.S.D.A. Zone 5.

2 Drawing Sheets

Botanical classification: *Lychnis sieboldii.*
Cultivar designation: 'Lipstick'.

BACKGROUND OF THE INVENTION

The present invention relates to a new and distinct cultivar of *Lychnis* plant, botanically known as *Lychnis sieboldii* 'Lipstick' and will be referred to hereafter by its cultivar name, 'Lipstick'. The new cultivar represents a new herbaceous perennial grown for landscape use.

The new cultivar derived from a controlled breeding program by the Inventor in Hubbardston, Mass. The objectives of the breeding program are to create new cultivars of *Lychnis* that are long lived, perform well in the garden, have large flowers in unique colors, and a sturdy well-branched plant habit.

The Inventor made a cross in 2002 between an unnamed proprietary plant in the Inventor's breeding program, reference no. 99-2, as the female parent and reference no. 99-18 as the male parent. The Inventor selected 'Lipstick' in July of 2004 as a single unique plant amongst the seedlings that resulted from the above cross.

Asexual propagation of the new cultivar was first accomplished by division in Hubbardston, Mass. in 2004 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Lipstick' as a unique cultivar of *Lychnis.*

1. 'Lipstick' exhibits sturdy erect stems up to 45 cm in height.
2. 'Lipstick' exhibits well-branched stems.

3. 'Lipstick' exhibits red flowers that are large in comparison to the species.
4. 'Lipstick' exhibits foliage that is red-purple in color when young and mature to dark green suffused with purple with the purple coloration maintained well into the season.
5. 'Lipstick' exhibits a long-lived habit; observed to live up to 10 years in Massachusetts without requiring division.
6. 'Lipstick' is reliably hardy at least in U.S.D.A. 5.

The species *Lychnis sieboldii* is endemic to Japan and is particularly hardy and long lived in comparison to related *Lychnis* species, hybrids and cultivars that are known to the Inventor. The Inventor is unaware of any other cultivars of *Lychnis sieboldii.* The female parent of 'Lipstick', 99-2, differs from 'Lipstick' in lacking sturdy stems (tend to lodge) and having few branches. The male parent of 'Lipstick', 99-18, differs from 'Lipstick' in having flowers that are salmon orange in color and in having green foliage that lacks any red-purple coloration. 'Lipstick' can be compared to cultivars of *Lychnis×arkwrightii* and *Lychnis chalcedonica. Lychnis×arkwrightii* differs from 'Lipstick' in having weak, floppy stems, smaller flowers, and in being shorter lived and less hardy. *Lychnis chalcedonica* differs from 'Lipstick' in having stems that are less branched and taller in height, foliage that is green and lacks red-purple coloration, and in having much smaller flowers.

BRIEF DESCRIPTION OF THE DRAWING

The accompanying colored photographs illustrate the overall appearance and distinct characteristics of the new *Lychnis.* The photographs were taken of two year-old plants as grown outdoors two-gallon containers in Hubbardston, Mass.

The photograph in FIG. 1 provides a close-up of the flower of 'Lipstick'.

Figure 1:
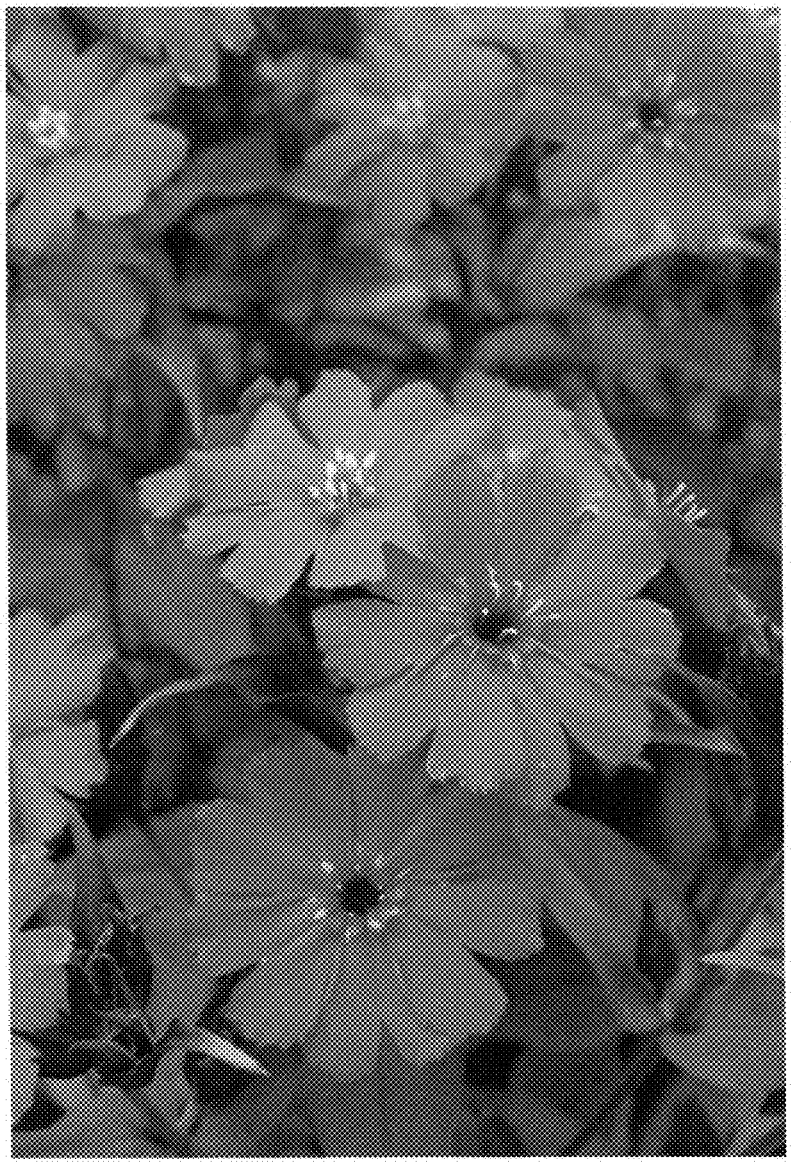
Figure 2:
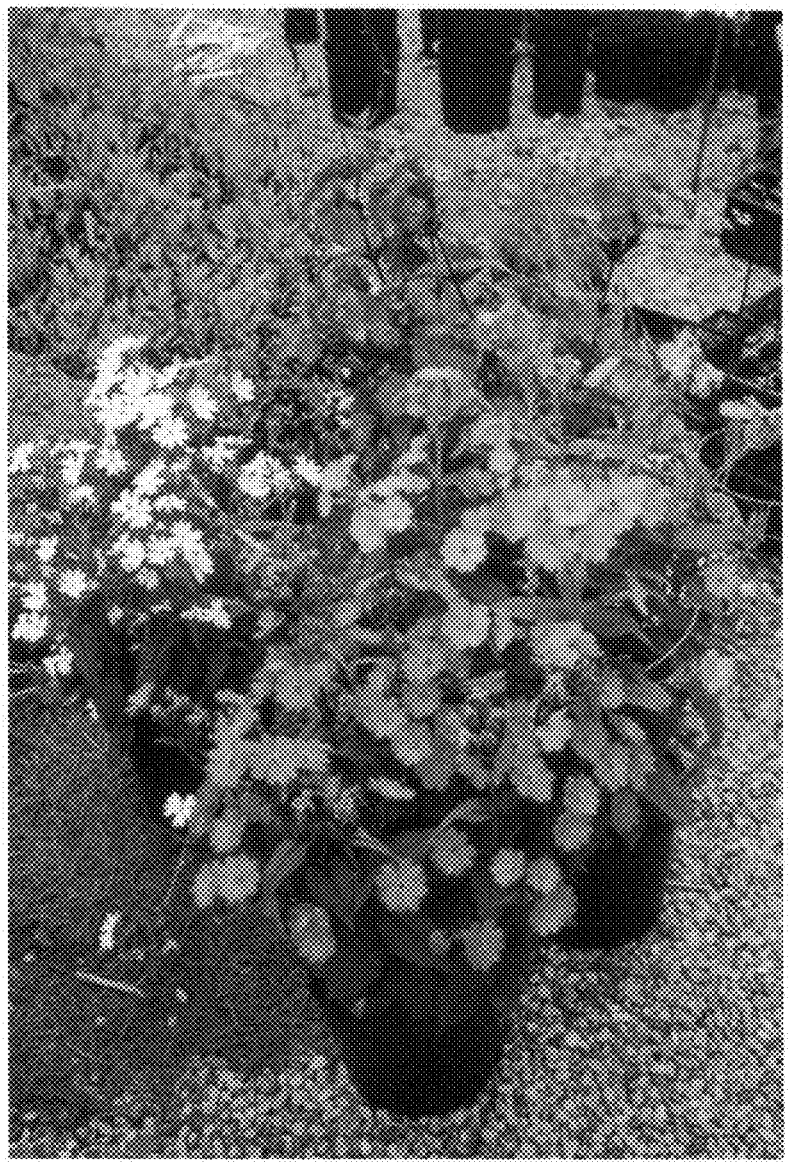

The photograph in FIG. 2 provides a view of 'Lipstick' in the front, the male parent directly behind it, the female parent in the back, and a plant of a white flowered *Lychnis sieboldii* on the left (to show the typical flower size of the species).

The colors in the photographs may differ slightly from the color values cited in the detailed botanical description, which accurately describe the colors of the new *Lychnis*.

DETAILED BOTANICAL DESCRIPTION OF THE PLANT

The following is a detailed description of two year-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—4 weeks from late June through July in Kensington, Conn.

*Plant habit.*—Herbaceous perennial, upright and slightly mounded with sturdy erect flowering stems.

*Height and spread.*—Reaches about 45 cm in height and 38 cm in spread.

*Cold hardiness.*—At least in U.S.D.A. Zone 5.

*Longevity.*—Has been shown to be long-lived without requiring division over a period of 10 years.

*Diseases and pests.*—No susceptibility or resistance to diseases or pests has been observed.

*Root description.*—Fine, fibrous.

*Growth rate.*—Moderate.

*Propagation.*—Division.

Stem description:

*Stem size.*—Flowering stem; up to 45 cm in length and 2 mm in width.

*Stem shape.*—Round.

*Stem color.*—Young stems; 145A, Mature stems; 187A.

*Stem surface.*—Slight sheen, base moderately covered in tomentulose hairs and becoming sparsely covered in tementulose hair at the top, hairs from mid to base 1 mm in length and NN155C in color, hairs from top to mid 0.3 mm in length and matches stem color.

*Stem aspect.*—Held nearly upright.

*Internode length.*—An average of 3 cm.

*Branching.*—Well-branched, about 9 branches per stem.

Foliage description:

*Leaf shape.*—Elliptic to oblanceolate.

*Leaf division.*—Simple.

*Leaf base.*—Cuneate.

*Leaf apex.*—Acute.

*Leaf venation.*—Pinnate, not conspicuous, mature veins 187A, young veins match leaf color.

*Leaf margins.*—Entire.

*Leaf attachment.*—Sessile.

*Leaf arrangement.*—Opposite.

*Leaf surface.*—Upper and lower surfaces rough to the touch, moderately to sparsely covered in stiff hairs, 0.3 mm in length and NN155C in color.

*Leaf color.*—Mature upper surface; closest to, but slightly darker than N139A, margins, veins and base 187A, mature lower surface; a blend of N199, 137A and 187A, young upper surface; 187A, young lower surface; a blend of 147A and 187A.

*Leaf size.*—Up to 7 cm in length and 3 cm in width when mature.

*Leaf quantity.*—An average of 14 per stem.

*Leaf fragrance.*—None.

Flower description:

*Inflorescence type.*—Single flowers at lateral nodes and corymbs on terminal of main stems.

*Lastingness of inflorescence.*—About 7 days dependent on climactic conditions.

*Inflorescence size.*—An average of 7 cm in height and 10 cm in diameter (when in corymbs).

*Flower fragrance.*—None.

*Flower number.*—Average of 3 per corymb, one corymb per flowering stem with 2 to 3 single flowers at upper nodes.

*Flower aspect.*—Upright to outward, dependant on location of the inflorescence.

*Flower bud.*—An average of 2.5 cm in length and 6 mm in width, oblong in shape with petal portion 45A in color and the sepal portion N77 with the margin of the very tips 144B.

*Flower form.*—Explanate.

*Flower size.*—Up to 5 cm in diameter and 4 cm in length.

*Flower bracts.*—An average of 6 per corymb, lanceolate in shape, up to 2.5 cm in length and 6 mm in width, truncate base, margins entire and ciliate, pubescent on upper and lower surfaces, color a blend of 177A and 144A on lower surface and 146A on upper surface.

*Calyx.*—Campanulate in form, comprised of fused sepals with sepal tips free, an average of 2 cm in length and 1 cm in width.

*Sepals.*—5, lanceolate in shape, occasionally overlapping, about 2 cm in length and 2 mm in width, base fused to tube, entire margins, outer and inner surface color; a blend of 144A and N77A in color, surface very finely puberulent on inner and outer surface.

*Corolla tube.*—Un-fused but arranged tube-like, about 1.9 cm in length and 1 cm in width, a blend of 14713 and 187A in color on inner and outer surface, very finely puberulent on outer surface.

*Petals.*—Partially overlapping, obcordate in shape with single deep notch, apex of segments are round and serrated, based fused to tube, margins on sides entire, an average of 1.5 cm in length and 1.5 cm in width, color of upper and lower surfaces 47B to 47C.

*Peduncles.*—Round in shape, an average of 1.5 cm in length and 3 mm in width, puberulent surface, a blend of 144A and N77A in color.

*Pedicels.*—Round in shape, an average of 1 cm in length and 1 mm in width, puberulent surface, a blend of 144A and N77A in color.

Reproductive organs:

*Gynoecium.*—1 pistil, stigma has 5 linear branches about 3 cm in length and 59B in color, style is about 2 cm in length, less than 1 mm in width, and 59B in color, homostylitic, ovary is inferior, 7 mm in length, 3 mm in width, oblong in shape and 144B in color.

*Androcoecium.*—10 stamens, anthers are dorsifixed, 2 mm in length and 11A in color, filaments are adnate to corolla, 3 mm in length, 0.5 mm in width, and 85D in color, pollen is abundant and 13A in color.

*Seeds.*—Not observed.

It is claimed:

1. A new and distinct cultivar of *Lychnis* plant named 'Lipstick' as herein illustrated and described.

* * * * *